US006277365B1

(12) United States Patent
Ellis et al.

(10) Patent No.: US 6,277,365 B1
(45) Date of Patent: *Aug. 21, 2001

(54) OPHTHALMIC COMPOSITION INCLUDING A CATIONIC GLYCOSIDE AND AN ANIONIC THERAPEUTIC AGENT

(75) Inventors: Edward James Ellis; Jeanne Yang Ellis, both of Lynnfield, MA (US)

(73) Assignee: Bausch & Lomb Incorporated, Rochester, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/932,676

(22) Filed: Sep. 18, 1997

(51) Int. Cl.$^7$ ..................................... A61K 31/74
(52) U.S. Cl. ........................ 424/78.04; 514/912
(58) Field of Search ................. 424/78.04; 514/912

(56) References Cited

U.S. PATENT DOCUMENTS

| | | | |
|---|---|---|---|
| 4,168,112 | 9/1979 | Ellis et al. | 351/160 |
| 4,767,463 | 8/1988 | Brode et al. | 106/162 |
| 4,913,743 | 4/1990 | Brode et al. | 106/162 |
| 5,077,033 | 12/1991 | Viegas et al. | 514/668 |
| 5,106,615 | 4/1992 | Dikstein | 424/78.04 |
| 5,138,043 | 8/1992 | Polovsky | 536/17.9 |
| 5,192,535 | 3/1993 | Davis et al. | 424/78.04 |
| 5,209,927 | 5/1993 | Gressel et al. | 424/78.04 |
| 5,358,706 | 10/1994 | Marlin et al. | 424/78.04 |
| 5,401,327 | 3/1995 | Ellis et al. | 134/42 |
| 5,405,878 * | 4/1995 | Ellis et al. | 422/28 |
| 5,461,081 | 10/1995 | Ali et al. | 514/772.3 |
| 5,521,222 | 5/1996 | Ali et al. | 514/772.5 |

* cited by examiner

Primary Examiner—Zohreh Fay
(74) Attorney, Agent, or Firm—Robert B. Furr, Jr.

(57) ABSTRACT

There are disclosed compositions and methods for treating the surface of the eye, or contact tenses to be placed on the eye, with an aqueous composition comprising a quaternary nitrogen-containing ethoxylated glycoside and a therapeutic agent. The subject invention is particularly suited for use with silicone-containing contact lenses. Examples of specific compositions include aqueous solutions of lauryl methyl gluceth-10 hydroxypropyl-dimonium chloride in combination with anionic polysaccharides such as hyaluronic acid.

26 Claims, No Drawings

OPHTHALMIC COMPOSITION INCLUDING A CATIONIC GLYCOSIDE AND AN ANIONIC THERAPEUTIC AGENT

FIELD OF THE INVENTION

The present invention relates to ophthalmic compositions containing a cationic glycoside in combination with a therapeutic agent. In particular, the cationic glycoside can be used to improve the efficacy of an anionic therapeutic agent or an anionic polymer delivery vehicle in combination with a therapeutic agent. The present composition can be applied to the eye or to a silicone-containing contact lens.

BACKGROUND

In general, the delivery of therapeutic substances to the surface of the eye has inherent difficulties because the washing action of the tear film removes much of the therapeutic substance. Typically, 90% or more of an ophthalmic drug in the form of an eye drop does not penetrate or adhere to the eye and is removed by tears through the lachrymal ducts.

Anionic therapeutic agents may lack affinity for the surface of an eye due to the anionic nature of the surface of the eye. Thus, the therapeutic effect provided by such agents may be short lived due to the rate at which the agent is flushed away from the eye. Attempts to solve this problem have resulted in the development of delivery systems for therapeutic agents. For example, U.S. Pat. No. 5,358,706 to Marlin et al. discloses a delivery system comprising a cationic polysaccharide in order to bind anionic therapeutic agents to the surface of the eye. Exemplary anionic therapeutic agents are glycosaminoglycans such as hyaluronic acid for the treatment of dry eye, as disclosed by Marlin et al. Synthetic anionic polymers have also been shown to be effective for the treatment of dry eye, for example, the carboxy vinyl polymers disclosed in U.S. Pat. No. 5,209,927 to Gressel et al. Combinations of cationic polymers (as delivery vehicles) with anionic therapeutic agents have also been used in the treatment of keratinous tissues such hair, skin and nails. See, for example, U.S. Pat. Nos. 4,913,743 and 4,767,463 to Brode et al.

U.S. Pat. No. 5,192,535 to Davis et al. discloses a topical ophthalmic medicament delivery method and system that employs carboxy vinyl polymers having certain physical properties that provide for the controlled, sustained release of medicaments after administration in drop form. The delivery system is designed to be administrable at a viscosity suitable for reliable drop dosages, but to substantially increase in viscosity after administration.

It is also possible to provide for the delivery of therapeutic agents with the aid of contact lenses as a delivery device, especially if the person being treated wears contact lenses anyway. Although not related to the delivery of a therapeutic agent, a variety of cationic compounds have been used to temporarily modify the surface properties of contact lenses. For example, cationic polymers have been used in aqueous compositions for lubricating and cushioning rigid gas permeable (RGP) lenses. Since RGP lenses typically have an anionically charged surface, cationic polymers tend to associate with the lens surface and can remain associated for an extended period of time. Examples of such cationic polymer are the cationic cellulosic polymers described in U.S. Pat. Nos. 4,168,112 and 5,401,327 to Ellis et al. As indicated above, U.S. Pat. No. 5,358,706 discloses similar cationic polymers as delivery vehicles for therapeutic agents.

Other cationic compounds have also been used to modify the surface properties of contact lenses. For example, quaternary nitrogen-containing ethoxylated glycosides are described in U.S. Pat. No. 5,405,878 to Ellis et al for use in contact-lens care solutions. These compounds each comprise a cationic hydrophobic moiety attached to an ammonium ion and a hydrophilic moiety consisting of a polyethoxylated glycoside derivative, preferably an alkylated glycoside. It is believed that the cationic moiety associates with the negatively charged surface of a lens, while the hydrophilic moiety extends from the lens surface to maintain moisture near the lens surface.

In administering therapeutic agents to the eye, a variety of factors, including consistency and accuracy of dosage, type and time of vision interference, ease of administration, and timing of delivery can be important. Prior ophthalmic delivery vehicles have suffered drawbacks in one or more respects and, in any case, improvement in performance is always desirable. New topical ophthalmic delivery systems for controlled, sustained release of therapeutic agents are, therefore, continually being developed. It is especially challenging to find an ophthalmic delivery vehicle that is safe and effective for human use and that does not have undesirable aide effects or cause undesirable interactions between components in a solution, particularly when limited to use in buffered solutions having osmolality values most common for in-eye solutions (typically from 270 to 330 mOsmols/kg).

SUMMARY OF THE INVENTION

The present invention provides a means for prolonging the association of a therapeutic agent with the surface of the eye and/or a contact lens in the eye, thereby increasing the beneficial effect offered by the therapeutic agent. In particular, the present invention utilizes quaternary nitrogen-containing ethoxylated glycosides to tether a therapeutic agent to the surface of the eye or to a contact lens. In one embodiment of the invention, the glycoside is used in combination with an anionic therapeutic agent. In a second embodiment of the invention, the glycoside is used in combination with both an anionic polymer and a therapeutic agent.

DETAILED DESCRIPTION OF THE INVENTION

As indicated above, the present invention is directed to ophthalmic compositions and their use for the treatment of eyes with therapeutic agents. The invention utilizes a cationic glycoside which is believed to act as a cationic tether, holding an anionic therapeutic agent, or an anionic delivery vehicle for a therapeutic agent, in association with the surface of the eye and/or a contact lens that is worn in the eye. The subject glycoside is non-polymeric and soluble in buffered aqueous solutions when combined with the subject anionic compounds, as described below.

The cationic glycosides employed in the present invention are described in detail in U.S. Pat. No. 5,405,878 which is incorporated herein by reference. These glycosides can be described as quaternary nitrogen-containing ethoxylated glycosides represented. A particularly preferred class of compounds is by Formula (I):

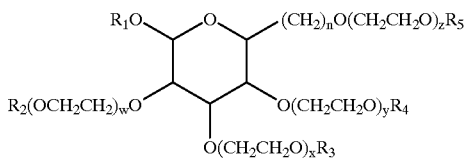

wherein $R_1$ is alkyl, preferably $C_1$–$C_{18}$; the average sum of w, x, y, and z per mole of compound is within the range of about 1 to about 200, preferably about 4 to about 20; n is 0 or 1; $R_2$, $R_3$, $R_4$, and $R_5$ are individually hydrogen or quaternary nitrogen-containing groups; provided that at least one of $R_2$, $R_3$, $R_4$, or $R_5$ is a quaternary nitrogen-containing group and that at least one of $R_2$, $R_3$, $R_4$, or $R_5$ is hydrogen. Representative quaternary nitrogen-containing groups for $R_2$, $R_3$, $R_4$, and $R_5$ are represented by Formula (II):

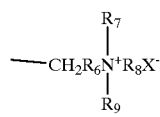

wherein $R_6$ is a $C_1$–$C_4$ hydroxyalkylene; $R_7$, $R_8$, and $R_9$ are an alkyl from $C_1$–$C_{16}$, and X is an anion, preferably a halide. Especially preferred compounds of Formula (I) include compounds wherein $R_1$ is methyl, each of $R_2$, $R_3$, and $R_4$ is hydrogen, and $R_5$ is a quaternary nitrogen-containing group as represented by Formula (II).

Such quaternary nitrogen-containing ethoxylated glycosides are commercially available or can be prepared by methods known in the art, such as the methods described in U.S. Pat. No. 5,138,043 to Polovsky et al. An especially preferred material is available under the CTFA designation lauryl methyl gluceth-10 hydroxypropyldimonium chloride, including the product commercially available under the tradename Glucquat-100® (from Amerchol Corp., Edison, N.J.).

The cationic glycoside of the present invention may be employed in the subject compositions at about 0.001 to about 10 weight percent, and preferably at about 0.001 to about 0.5 weight percent.

As mentioned above, the subject glycoside-containing compositions may be used in the treatment of the eye with a therapeutic agent, including both ophthalmic drugs and dry-eye agents. In particular, the subject glycosides are especially effective in prolonging the effect of anionic therapeutic agents that adhere to, or associate with, the eye and/or a contact lens by means of the subject cationic glycosides. Examples of preferred anionic therapeutic agents are anionic polysaccharides, including glycosaminoglycans such as hyaluronic acid and derivatives thereof and/or salts thereof, chondroitin sulfate, carboxymethylcellulose (CMC), and algin. Various glycosaminoglycans are listed in U.S. Pat. No. 5,358,706, hereby incorporated by reference. Hyaluronic acid is an anionic biopolymer that has been identified as useful in the treatment of the symptoms of dry eye. Synthetic anionic polymers for the treatment of dry eye can also be used in combination with the above-described glycoside, including the carboxy vinyl polymers known as Carbopol,® commercially available from B.F. Goodrich, as described in U.S. Pat. No. 5,209,927 to Gressel et al.

The glycoside and the anionic therapeutic agent used in the present composition are soluble in buffered aqueous solutions which have osmolality values in the range of about 250 to about 350 mOsmols/kg.

Compositions of the present invention typically include from about 0.0001 to about 5 weight percent, and preferably from 0.01 to 2.0 weight percent, based on the total weight of the composition of at least one therapeutic agent. The ratio of the glycoside to the therapeutic agent may vary widely. Generally an effective amount, which is defined as the amount of the glycoside sufficient to provide substantivity to a contact lens and/or the mucosal surface of the eye. In general, the relative weight ration of glycoside to therapeutic agent may range from 0.01:1 to about 200:1.

In still another embodiment of the invention, a cationic glycoside may be combined with an anionic polymeric carrier or delivery vehicle that promotes a sustained or delayed release of an ophthalmic drug. Such anionic polymers include carboxy containing polymers, for example, as disclosed in U.S. Pat. No. 5,192,535 to Davis et al. and U.S. Pat. No. 5,461,081 to Ali et al., the disclosures of both hereby incorporated by reference. Preferred anionic polymeric carrier are the carboxy vinyl polymers available from B.F. Goodrich under the product name Carbopol®. Such polymers may be used in combination with oppositely charged electrolytes as disclosed in U.S. Pat. No. 5,521,222. Combinations of polymers may be employed, as disclosed in U.S. Pat. No. 5,077,033. The composition may be in the form of a solution or gel.

The amount of the anionic polymer in the composition may also vary widely. Typically, the amount of the polymer is at least about 0.0005 weight percent, preferably from about 0.00025 to about 20.0 weight percent, and most preferably from about 0.005 to 10 weight percent. The amount, however, will depend on whether other polymers are included and whether the composition is in the form of a gel or solution and the specific method of topical application to the eye.

The present invention may be practiced in a number of different embodiments. In one embodiment, a composition according to the present invention is applied to a contact lens, either before or after the lens is placed in the eye. In particular, the present invention is suitable for application to a silicone-containing lens, either a rigid gas permeable (RGP) lens or a high Dk (extended wear) silicone-containing hydrogel lens. An example of a silicone-containing hydrogel material is disclosed in U.S. Pat. No. 5,260,000.

The composition may be applied to a lens before the lens is placed in the eye. Optionally, the lens can be first contacted with an aqueous solution of the subject cationic glycosides to form a thin cationic coating on the lens surface and subsequently contacted with an aqueous solution of one or more anionic therapeutic agents, or an anionic delivery vehicle in combination with one or more therapeutic agents, thus forming an outer anionic coating on the lens surface. Alternatively, a contact lens can be treated with an aqueous composition comprising a mixture of a cationic glycoside and one or more anionic therapeutic agents or a mixture of a cationic glycoside, an anionic delivery vehicle, and one or more therapeutic agents. Such compositions may, of course, include other conventional or monographed constituents such as thickeners, comfort agents, and stabilizers, including polyols such as glycerin.

Contact lenses may be contacted or treated with the subject compositions in the form of an aqueous solution, for example, by storing or soaking the contact lens in the solution or by spraying the lens with the solution for sufficient time to wet the surfaces thereof. The treated lens can be placed directly in the eye or, alternatively, the lens can be first rinsed before being placed in the eye. Drops of subject solution can be placed on the lens surface and the treated lens placed in the eye, or the subject composition may be directly applied to the eye in the form of eye-drops while the contact lens is being worn. The specific lens care regimen used may depend on the other compounds or ingredients present in the solution, as will be appreciated by those skilled in the art.

In another embodiment of the invention, a composition according to the present invention is placed or instilled directly in the eye, for example, by means of eye drops independent, or in the absence, of contact lenses. In this embodiment, the anionic surface of the eye, especially the cornea, is the target for adherence of the cationic glycoside.

By the term "therapeutic agents" herein is broadly meant ingredients which treat, diagnose, or prevent disorders or diseases of the eye. Therapeutic agents include agents such as lubricants or humectants that can treat or alleviate the symptoms of dry eye, as well as ophthalmic drugs. Ophthalmic drugs that may be used in compositions according to the present invention include known or conventional anti-inflammatory agents, anti-infection agents, glaucoma agents, imaging agents, and wound-healing agents. Illustrative anionic drugs that can be combined with the subject glycoside include, as listed in U.S. Pat. No. 5,358,706 to Marlin et al., anti-inflammatory agents such as prostaglandins and derivatives, salicylic acid, proprionic acid, fenemates such as anthranilic acid derivatives and cromolyn; anti-infective agents such as beta lactam antibiotics, glaucoma agents such as carbonic anhydrase inhibitors, imaging agents such as fluorescein and derivatives, and wound healing agents such as peptide growth factors. In embodiments employing an anionic delivery vehicle, it is not necessary to limit the therapeutic agent to anionic compounds and illustrative drugs include antibiotics, antivirals, steroids, aminosubstituted steroids, polypeptides, cardiotonics, anti-hypertensives, anti-allergics, alpha- and beta-adrenergic blocking agents, anti-cataract agents, anti-glaucoma agents, anti-inflammatory agents, and anesthetic agents. Examples of specific drugs are listed in U.S. Pat. No. 5,192,535 to Davis et al., hereby incorporated by reference. Therapeutic agents or their pharmaceutically acceptable salt may be used.

Yet another aspect of the present invention is directed to a method for treating dry eye comprising topically administering to the eye of a patient suffering from dry eye a composition comprising a therapeutically effective amount of a sterile, aqueous composition comprising 0.001 to 10 percent by weight of the composition of a quaternary nitrogen-containing ethoxylated glycoside in combination with an effective amount of an anionic polymer that is a therapeutic agent effective in treating dry eye or keratoconjunctivitis sicca. The method preferably involves applying a solution or gel of the composition directly to the eye, preferably in the form of eye drops, either in the presence or the absence of a contact lens in the eye. Alternatively, a contact lens may be contacted with the composition before the contact lens is placed in the eye. The anionic polymer may be a polysaccharide, preferably a glycosaminoglycan such as hyaluronic acid, xanthan gum, or derivatives and/or salts of the foregoing. Alternatively, the anionic polymer may be a suitable synthetic polymer selected from the group consisting of carbomers and polyacrylic acids. Examples of such therapeutic agents can be found, for example, in U.S. Pat. No. 5,106,615 to Dickstein et al. and numerous other patents and literature references. Examples of polysaccharides may be found, for example, in IL FARMACO, 50 (9), 633–642 (1995), in the article by Albasini, Marco et al.

Compositions of the present invention may include additional constituents. For example, typical compositions include buffering agents for buffering or adjusting the pH of the composition, and/or tonicity adjusting agents for adjusting the tonicity (osmolality) of the composition. Preferably, the pH of compositions according to the present invention, which may be in the form of a solution or gel, should be maintained within the range of 5.0 to 8.0, more preferably 6.0 to 8.0, most preferably 6.5 to 7.8. Representative buffering agents include alkali metal salts such as potassium or sodium carbonates, acetates, borates, phosphates, citrates, and hydroxides; and weak acids such as acetic, boric, and phosphoric acids. Representative tonicity adjusting agents include sodium and potassium chloride, and those materials listed as buffering agents. Generally, buffers will be present in amounts ranging from about 0.05 to 2.5 percent by weight of the composition, preferably from 0.1 to 15 percent. The tonicity agents may be employed in an amount effective to adjust the osmotic value of the final composition to a desired value, typically from about 250 to about 350 mOsmols/kg in order to approximate the osmotic pressure of normal lachrymal fluids which is equivalent to a 0.9 percent solution of sodium chloride. Generally, the buffering agents and/or tonicity adjusting agents may be included up to about 10 weight percent.

In some embodiments, an antimicrobial agent is included in the composition in an antimicrobially effective amount, i.e., an amount which is effective to at least inhibit growth of microorganisms in the composition. The composition can be used to also disinfect a contact lens treated therewith. Various antimicrobial agents are known in the art as useful in contact lens solutions, including chlorhexidine (1,1'-hexamethylene-bis[5-(p-chlorophenyl)biguanide]) or water soluble salts thereof, such as chlorhexidine gluconate; polyhexamethylene biguanide (a polymer of hexamethylene biguanide, also referred to as polyaminopropyl biguanide) or water-soluble salts thereof such as the a polyhexamethylene biguanide hydrochloride available under the trade name Cosmocil CQ (ICI Americas Inc.); benzalkonium chloride; and polymeric quaternary ammonium salts. When present, the antimicrobial agent may be included at 0.00001 to about 5 weight percent, depending on the specific agent.

The compositions may further include a sequestering agent (or chelating agent) which can be present up to about 2.0 weight percent. Examples of preferred sequestering agents include ethylenediaminetetraacetic acid (EDTA) and its salts, with the disodium salt (isodium edetate) being especially preferred.

In order that those skilled in the art can more fully appreciate the aspects of the invention, the following examples are set forth, which examples are given solely for purposes of illustration, and should not be considered as expressing limitations unless so set forth in the appended claims.

EXAMPLES

In the following examples, blanks of a commercial fluorosilicone rigid gas permeable contact lens material (Boston RXD® available from Polymer Technology Corporation of Wilmington, Mass.) were formulated without wetting agents. These, blanks were cut into wafers and both sides were polished to an optical finish. The wafers were then soaked in deionized water overnight, and subsequently treated with various aqueous solutions as described below. After each treatment with a solution, dynamic contact angle and surface tension measurements were taken using a Cahn Instrument DCA 322. The results are provided below. A baseline aqueous buffer solution used in each of the examples below consisted of a phosphate buffer prepared comprising 0.280% sodium phosphate (dibasic), 0.055% potassium phosphate (monobasic), 0.780% sodium chloride, 0.170% potassium chloride, 0.050% disodium edetate, and a sufficient amount of deionized water to bring the total percent to 100. Al percentages are weight percent, unless otherwise indicated. The abbreviations used in the Tables below have the following meanings:

S.T.=Surface Tension (dynes/cm).

Adv=Advancing contact angle in degrees.

Rec=Receding contact angle in degrees.

Adv-Rec=Difference between advancing and receding contact angles.

EXAMPLE 1

This example illustrates the abiity of a cafionic glycoside to tether an anionic polymer (xanthan gum) to the surface of a contact-lens material. Xanthan gum is usefull either as a vehicle for an ophthalmic drug or as a therapeutic agent for the treatment of the symptoms of dry eye. The following three solutions were prepared by adding a sufficient amount of the indicated constituent to the baseline phosphate buffer (described above) in order to achieve the final percentage indicated: (1) 0.015% Glucquat® 100 glycoside; (2) 0.015% xanthan gum; and (3) a mixture of 0.015% Glucquat® 100 glycoside and 0.015% xanthan gum. (Glucquat® 100 is a registered trademark of Amerchol for lauryl methyl gluceth-10 hydroxypropyldimonium chloride.) The above-described wafers were sequentially dipped within the solutions indicated in the Tables 1-1 through 1-4. After being treated with each solution, contact angle measurements were taken, the results of which are also provided in the Tables below.

TABLE 1-1

| Condition | 1<br>Phosphate<br>Buffer | 2<br>0.015%<br>Glycoside | 3<br>1st Desorption in<br>Buffer | 4<br>2nd Desorption<br>in Buffer |
| --- | --- | --- | --- | --- |
| S.T. | 73.4 | 43.1 | | |
| Adv | 102 | 76 | 102 | 102 |
| Rec | 58 | 20 | 55 | 55 |
| Adv-Rec | 44 | 56 | 47 | 47 |

It is evident from the lowering of the surface tension that the Glucquat® 100 glycoside is very surface active. Furthermore, lens treatment with Glucquat® 100 dramatically lowered both the advancing and receding contact angles of the treated wafers (see Condition 2). However, the adsorbed Glucquat® on the wafer surface is almost entirely removed during the first and second desorption processes (i.e. dipping the wafer in fresh buffer solutions) in that the wafer surface returns to baseline values (see Conditions 3 and 4 as compared to Condition 1 in Table 1-1).

TABLE 1-2

| Condition | 1<br>Phosphate<br>Buffer | 2<br>0.015%<br>Xanthan<br>Gum | 3<br>1st Desorption in<br>Buffer | 4<br>2nd Desorption in<br>Buffer |
| --- | --- | --- | --- | --- |
| S.T. | 73.4 | 72.3 | | |
| Adv | 103 | 100 | 100 | 101 |
| Rec | 59 | 48 | 50 | 51 |
| Adv-Rec | 44 | 52 | 50 | 50 |

As evident from Table 1-2 above, the surface tension of the xanthan gum solution is very close to that of the baseline phosphate buffer solution. Furthermore, the xanthan solution did not significantly lower advancing angles and had only a minor reducing effect on the receding contact angles. Given the data of Table 1-2, it would appear that the xanthan solution had little affinity for the wafer surface.

TABLE 1-3

| Condition | 1<br>Phosphate<br>Buffer | 2<br>0.015%<br>Glycoside | 3<br>0.015%<br>Xanthan<br>Gum | 4<br>1st<br>Desorption<br>in Buffer | 5<br>2nd<br>Desorption<br>in Buffer |
| --- | --- | --- | --- | --- | --- |
| S.T. | 73.4 | 43.1 | 72.8 | | |
| Adv | 103 | 76 | 61 | 45 | 44 |
| Rec | 59 | 20 | 37 | 19 | 19 |
| Adv-Rec | 44 | 56 | 24 | 26 | 25 |

As indicated in Table 1-3 above, while the Glucquat 100® glycoside is very surface active, once the Glucquat® has been adsorbed onto the surface, exposure to an xanthan gum solution (Condition 3) appears to result in the formation of a complex on the surface wherein the receding angle is raised due to the presence of the xanthan gum polymer. The advancing/receding angles are significantly lowered in both cycles of desorption process, indicating that this surface complex is very tenacious (Conditions 4 and 5 in Table 1-3 above).

TABLE 1-4

| Condition | 1<br>Phosphate<br>Buffer | 2<br>0.015% Glycoside<br>plus 0.015%<br>Xanthan Gum ® | 3<br>1st<br>Desorption<br>in Buffer | 4<br>2nd<br>Desorption<br>in Buffer |
| --- | --- | --- | --- | --- |
| S.T. | 73.4 | 47.2 | | |
| Adv | 103 | 41 | 89 | 90 |
| Rec | 59 | 31 | 28 | 31 |
| Adv-Rec | 44 | 10 | 61 | 59 |

As indicated in Table 1-4 above, combining the Glucquat® glycoside and xanthan gum in the same solution produces a complex that exhibits surface activity as evidenced by the low surface-tension values. This complex adsorbs onto the wafer surface and lowers both the advancing and receding angles (Condition 2). This surface complex is very tenacious, and the receding angles in both cycles of the desorption process are stable (Condition 3 and 4).

EXAMPLE 2

This example illustrates the ability of a cationic glycoside to tether an anionic polymer (a carboxy vinyl polymer) to the surface of a contact lens material. Such polymers are useful either as a vehicle for an ophthalmic drug or as a therapeutic agent for the treatment of the symptoms of dry eye. The following three solutions were prepared by adding a sufficient amount of the indicated constituent to the baseline phosphate buffer (described above) in order to achieve the final percentage indicated: (1) 0.015% Carbopol® 971P polymer, (2) 0.015% Glucquat® 100 glycoside, and (3) a mixture of 0.015% Glucquat® 100 and 0.015% Carbopol® 971P. (Carbopol® is a trademark of B.F. Goodrich for carbomer that is a homopolymer of acrylic acid crosslinked with an allyl ether of pentaerythritol or an allyl ether of sucrose.)

The above-described wafers were sequentially dipped within the solutions indicated in the Tables 2-1 through 2-3 below in the same manner described with respect to Example 1. After being treated with each solution, contact angle measurements were taken, the results of which are also provided in the Tables below.

TABLE 2-1

| Condition | 1 Phosphate Buffer | 2 0.015% Carbomer | 3 1st Desorption in Buffer | 4 2nd Desorption in Buffer |
|---|---|---|---|---|
| S.T. | 73.2 | 72.0 | | |
| Adv | 104 | 103 | 103 | 103 |
| Rec | 55 | 52 | 52 | 53 |
| Adv-Rec | 49 | 51 | 51 | 50 |

As indicated in Table 2-1 above, the surface tension of the 0.015% Carbopol® 971P carbomer solution is very close to that of the baseline phosphate buffer solution. A concentration of 0.015% carbomer did not lower the advancing and the receding contact angles of the wafers (Condition 2 in Table 2-1). This data suggest that there was only slight or no affinity of the carbomer to the non-wetting wafer surfaces. Also both the first and the second desorption process exhibit close to baseline conditions (Conditions 3 and 4).

TABLE 2-2

| Condition | 1 Phosphate Buffer | 2 0.015% Glyco-side | 3 0.015% Carbomer | 4 1st Desorption in Buffer | 5 2nd Desorption in Buffer |
|---|---|---|---|---|---|
| S.T. | 73.2 | 43.1 | 72.0 | | |
| Adv | 103 | 75 | 84 | 90 | 91 |
| Rec | 53 | 21 | 33 | 36 | 37 |
| Adv-Rec | 50 | 56 | 51 | 54 | 54 |

As indicated in Table 2-2 above, once the glycoside (Glucquat® 100) has been adsorbed on the surface, exposure to the carbomer (Carbopol® 971P) solution indicates the formation of a complex on the surface in that both the advancing and the receding angles are raised due to the presence of the carbomer polymer (Condition 3). In the desorption process, both cycles, indicated that the surface complex is very tenacious in that the advancing/receding angles angles stable (Conditions 4 and 5).

TABLE 2-3

| Condition | 1 Phosphate Buffer | 2 0.015% Glycoside plus 0.015% Carbomer | 3 1st Desorption in Buffer | 4 2nd Desorption in Buffer |
|---|---|---|---|---|
| S.T. | 73.2 | 45.9 | | |
| Adv | 103 | 25 | 86 | 88 |
| Rec | 54 | 22 | 30 | 29 |
| Adv-Rec | 49 | 3 | 56 | 59 |

As indicated in Table 2-3 above, combining a glycoside (Glucquat® 100) and a carbomer (Carbopol® 971P) in the same solution produces a complex that exhibits surface activity as evidenced by the low surface tension. The complex adsorbs onto the non-wetting wafer surface as evidenced by the low advancing and receding angles (Condition 2). The complex desorbs very slowly from the wafer surface (Conditions 3 and 4).

EXAMPLE 3

This example illustrates the ability of a cationic glycoside to tether an anionic polymer (hyaluronic acid) to the surface of a contact lens material. Such polymers are particularly useful as a therapeutic agent for the treatment of the symptoms of dry eye. The following three solutions were prepared by adding a sufficient amount of the indicated constituent to the baseline phosphate buffer (described above) in order to achieve the final percentage indicated: (1) 0.015% hyaluronic acid, (2) 0.015% Glucquat® 100 glycoside, and (3) a mixture of 0.015% Glucquat® 100 and 0.015% hyaluronic acid.

The above-described wafers were sequentially dipped within the solutions indicated in the Tables 3-1 through 3-3 below in the same manner as described with respect to Example 1. After being treated with each solution, contact angle measurements were taken, the results of which are also provided in the Tables below.

TABLE 3-1

| Condition | 1 Phosphate Buffer | 2 0.015% Hyaluronic acid | 3 1st Desorption in Buffer | 4 2nd Desorption in Buffer |
|---|---|---|---|---|
| S.T. | 73.4 | 72.3 | | |
| Adv | 102 | 100 | 101 | 101 |
| Rec | 56 | 55 | 56 | 57 |
| Adv-Rec | 46 | 45 | 45 | 44 |

As indicated in Table 3-1 above, the surface tension of the 0.015% hyaluronic acid solution is very close to that of the baseline phosphate buffer solution. A concentration of 0.015% hyaluronic acid did not lower the advancing and the receding contact angles of the wafers (Condition 2). This suggests that there was only slight or no affinity of hyaluronic acid to the non-wetting wafer surfaces. Also both the first and the second desorption process exhibit close to baseline conditions (Conditions 3 and 4).

TABLE 3-2

| Condition | 1 Phosphate Buffer | 2 0.015% Glyco-side | 3 0.015% Hyaluronic acid | 4 1st Desorption in Buffer | 5 2nd Desorption in Buffer |
|---|---|---|---|---|---|
| S.T. | 73.4 | 43.1 | 72.3 | | |
| Adv | 102 | 77 | 83 | 94 | 94 |
| Rec | 59 | 18 | 39 | 38 | 39 |
| Adv-Rec | 43 | 59 | 44 | 56 | 55 |

As indicated in Table 3-2 above, once the glycoside (Glucquat® 100) has been adsorbed on the surface of the lens material wafer, exposure to a hyaluronic acid solution indicates the formation of a complex on the surface in that both the advancing and the receding angles are raised due to the presence of the hyaluronic acid (Condition 3 in the Table). In the desorption process, both cycles indicated that the surface complex is very tenacious in that the advancing/receding angles are stable (Conditions 4 and 5).

TABLE 3-3

| Condition | 1 Phosphate Buffer | 2 0.015% Glycoside plus 0.015% Hyaluronic acid | 3 1st Desorption in Buffer | 4 2nd Desorption in Buffer |
|---|---|---|---|---|
| S.T. | 73.4 | 45.5 | | |
| Adv | 102 | 35 | 93 | 95 |
| Rec | 55 | 20 | 41 | 42 |
| Adv-Rec | 47 | 15 | 52 | 53 |

As indicated in Table 3-3 above, combining a glycoside (Glucquat® 100) with hyaluronic acid in the same solution produces a complex that exhibits surface activity as evidenced by the low surface tension. The complex adsorbs onto the non-wetting wafer surface as evidenced by the low advancing and receding angles (Condition 2 in the Table). The complex desorbs very slowly from the wafer surface (Conditions 3 and 4).

EXAMPLE 4

This example illustrates the preparation of formulations for the treatment of the symptoms of dry eye. Three formulations (Test Solutions 1-3) were prepared using the ingredients listed below in Table 4. Boston® IV and Boston RXD® lenses were soaked overnight in these test solutions. The lenses were subsequently worn by patients who were then examined by a clinician using a biomicroscope. The solutions were all found to provide a conditioned lens surface which exhibited excellent ocular compatibility. The tear film wetted the entire surface of the lenses and was even in nature. Furthermore, the relative thickness of tear film was increased, indicating that the test solutions could be used for treating or relieving the symptoms of dry eye or to provide an artificial tear.

TABLE 4

| CONSTITUENT | Test Solution 1 | Test Solution 2 | Test Solution 3 |
| --- | --- | --- | --- |
| carbomer (Carbopol ® 971P) | 0.5 | | |
| hyaluronic acid | | | 0.15 |
| xanthan | | 0.3 | |
| glycoside (Glucquat 100 ®) | 0.01 | 0.01 | 0.01 |
| sodium chloride | 0.45 | 0.45 | 0.85 |
| sodium borate | 0.90 | 0.90 | |
| boric acid | 0.10 | 0.10 | |
| polyhexamethylene biguanide | 15 (ppm) | 15 | |
| sodium phosphate, dibasic | | | 0.04 |
| potassium phosphate, monobasic | | | 0.005 |
| deionized water (Q.S.) | 100 | 100 | 100 |

Based upon the foregoing, it should be apparent to those skilled in the art that the present invention is not limited by the examples set forth above and that the use of specific compositions can be determined from the specification without departing from the invention as herein disclosed and described. It should be understood that the scope of the present invention includes all modifications and variation that fall within the scope of the attached claims.

What is claimed is:

1. A method for delivering an anionic therapeutic agent to an eye which method comprises applying topically to the eye a therapeutically effective amount of a sterile, aqueous composition, said composition comprising:
    (a) an effective amount of the anionic therapeutic agent,
    (b) an amount of a quaternary nitrogen-containing ethoxylated glycoside in the range of from 0.001 to 10 percent by weight of the composition to hold said anionic therapeutic agent in association with the surface of the eye or a contact lens worn in the eye.

2. The method of claim 1, wherein the composition is a solution that is applied directly to the eye in the form of eye drops, either in the presence or the absence of a contact lens in the eye.

3. The method of claim 1, wherein a contact lens is contacted with said composition and the contact lens is then placed in the eye.

4. The method of claim 1, wherein a contact lens is contacted with said contact lens by sequentially contacting the lens with a solution of the glycoside and a solution of the therapeutic agent, thereafter placing the contact lens in the eye.

5. The method of claim 1 wherein the anionic therapeutic agent is an anionic polysaccharide or a carboxy-containing polymer.

6. The method of claim 1 wherein the anionic therapeutic agent is hyaluronic acid or a derivative thereof and/or salts thereof.

7. A method for the treatment of dry eye or, with an ophthalmic drug, treating, preventing, or diagnosing disorders or diseases of the eye, which method comprises the delivery of an anionic therapeutic agent to an eye by applying an aqueous composition topically to the eye, said aqueous composition comprising:
    (a) an effective amount of therapeutic agent,
    (b) an effective amount of a delivery vehicle comprising an anionic polymer; and
    (c) 0.001 to 10 percent by weight of the composition of a quaternary nitrogen-containing ethoxylated glycoside to hold said therapeutic agent in association with the surface of the eye or a contact lens worn in the eye.

8. The method of claim 7, wherein the composition, in the form of a solution or gel, is applied directly to the eyes.

9. The method of claim 7, wherein a contact lens is contacted with the composition and the contact lens is then placed in the eye.

10. The method of claim 7, wherein the anionic polymer delivery vehicle is a carboxy-containing polymer.

11. A method for treating dry eye comprising topically administering to an eye of a patient suffering from dry eye a composition comprising a therapeutically effective amount of a sterile, aqueous composition, said composition comprising:
    (a) 0.001 to 10 percent by weight of the composition of a quaternary nitrogen-containing ethoxylated glycoside,
    (b) an effective amount of an anionic polymer effective in treating dry eye.

12. The method of claim 11, wherein the solution is applied directly to the eye either in the presence or the absence of a contact lens in the eye.

13. The method of claim 11, wherein a contact lens is contacted with said composition and the contact lens is then placed in the eye.

14. The method of claim 11, wherein the anionic polymer is a polysaccharide.

15. The method of claim 14, wherein the anionic polymer is a glycosaminoglycan.

16. The method of claim 15, wherein the anionic polymer is a biopolymer selected from the group consisting of hyaluronic acid, xanthan gum, and derivatives and salts thereof.

17. The method of claim 11, wherein the anionic polymer is a synthetic polymer selected from the group consisting of carbomers and polyacrylic acids.

18. A method for increasing the beneficial effect of an anionic therapeutic agent in an eye comprising prolonging the association of the therapeutic agent with the surface of the eye by administering an effective amount of a sterile, aqueous composition, said composition comprising the anionic therapeutic agent in combination with an amount of a quaternary nitrogen-containing ethoxylated glycoside in the range of from 0.001 to 10 percent by weight of the composition to hold said anionic therapeutic agent in association with the surface of the eye or a contact lens worn in the eye.

19. The method of claim 18, wherein the composition is a solution that is applied directly to the eye in the form of eye drops, either in the presence or the absence of a contact lens in the eye.

20. The method of claim 19, wherein a contact lens is contacted with said composition and the contact lens is then placed in the eye.

21. The method of claim 20, wherein a contact lens is contacted with said contact lens by sequentially contacting the lens with a solution of the glycoside and a solution of the therapeutic agent, thereafter placing the contact lens in the eye.

22. The method of claim 21 wherein the anionic therapeutic agent is an anionic polysaccharide or a carboxy-containing polymer.

23. The method of claim 22 wherein the anionic therapeutic agent is hyaluronic acid or a derivative thereof and/or salts thereof.

24. The method of claim 22 wherein the anionic therapeutic agent is at one ophthalmic drug selected from the group consisting of anti-inflammatory agents, anti-infection agents, glaucoma agents, imaging agents, and wound-healing agents.

25. The method of claim 24 wherein the ophthalmic drug is at least one selected from the group consisting of prostaglandins, prostaglandin derivatives, salicylic acid, proprionic acid, fenemates including anthranilic acid derivatives and cromolyn, beta lactam antibiotics, carbonic anhydrase inhibitors, fluorescein, fluorescein derivatives, and peptide growth factors.

26. The method of claim 25 wherein the ophthalmic drug is at least one selected from the group consisting of antibiotics, antivirals, steroids, aminosubstituted steroids, polypeptides, cardiotonics, anti-hypertensives, anti-allergics, alpha- and beta-adrenergic blocking agents, anti-cataract agents, anti-glaucoma agents, anti-inflammatory agents, and anesthetic agents.

* * * * *